United States Patent
Farrar-Gaines et al.

(10) Patent No.: US 11,418,900 B2
(45) Date of Patent: Aug. 16, 2022

(54) DEVICE FOR UNOBTRUSIVE TREATMENT OF TINNITUS

(71) Applicant: The Johns Hopkins University, Baltimore, MD (US)

(72) Inventors: Dawnielle Farrar-Gaines, Reisterstown, MD (US); Bradford J. May, Glen Arm, MD (US); Howard W. Francis, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 620 days.

(21) Appl. No.: 16/506,595

(22) Filed: Jul. 9, 2019

(65) Prior Publication Data

US 2020/0021929 A1  Jan. 16, 2020

Related U.S. Application Data

(60) Provisional application No. 62/696,070, filed on Jul. 10, 2018.

(51) Int. Cl.
| | |
|---|---|
| *H04R 25/00* | (2006.01) |
| *H04R 1/10* | (2006.01) |
| *A61F 11/00* | (2022.01) |
| *H04R 17/00* | (2006.01) |

(52) U.S. Cl.
CPC .............. *H04R 25/75* (2013.01); *A61F 11/00* (2013.01); *H04R 1/1016* (2013.01); *H04R 17/005* (2013.01); *H04R 2460/09* (2013.01)

(58) Field of Classification Search
CPC ... H04R 25/45; H04R 1/1016; H04R 2460/17
USPC .......................................... 381/317, 328–329
See application file for complete search history.

(56) References Cited

U.S. PATENT DOCUMENTS

| | | | |
|---|---|---|---|
| 8,641,919 B2 | 2/2014 | Yu et al. | |
| 9,484,524 B2 | 11/2016 | Yu et al. | |
| 2010/0061580 A1* | 3/2010 | Tiscareno | ............ H04R 1/1016 381/380 |
| 2016/0030245 A1* | 2/2016 | Perry | ................. A61N 1/36132 600/28 |

\* cited by examiner

*Primary Examiner* — George C Monikang
(74) *Attorney, Agent, or Firm* — Todd Farnsworth

(57) ABSTRACT

A tinnitus treatment device may include a sound generation unit configured to generate an electrical stimulus, and an open earphone operably coupled to the sound generation unit to produce acoustic vibrations based on the electrical stimulus. The open earphone may include an auditory passage and the open earphone may be insertable into an ear canal of a person such that the auditory passage enables sound to pass substantially unobstructed by the device into the ear canal of the person. The sound generation unit may be configured to be adjustable to tune the electrical stimulus based on a characteristic of tinnitus symptoms experienced by the person.

20 Claims, 5 Drawing Sheets

DEVICE FOR UNOBTRUSIVE TREATMENT OF TINNITUS

CROSS-REFERENCE TO RELATED APPLICATIONS

This application claims the benefit of U.S. Provisional Application No. 62/696,070, filed on Jul. 10, 2018, the entire contents of which are hereby incorporated herein by reference.

TECHNICAL FIELD

Example embodiments of the present disclosure generally relate to hearing improvement technology, and more specifically relate to a device that can be used to minimize the impact of tinnitus, while remaining unobtrusive and avoiding interference with environmental awareness while the device is being used.

BACKGROUND

Over 45 million Americans experience tinnitus each year. Of those, about 20 million seek medical attention and about 2 million suffer to such a degree that they cannot lead normal lives. Tinnitus cannot be cured by drugs, surgery or prosthetics. Thus, the most common intervention has been made in the area of suppression. The devices that are typically used for suppression resemble conventional hearing aids in that they are inserted into the ear and block the ear canal. However, unlike a conventional hearing aid, which receives and amplifies the sound otherwise heading into the ear canal, devices aimed at treating tinnitus deliver a masking sound into the ears in order to cover up the unrelenting effects of tinnitus.

This masking process generally provides relief to most tinnitus patients. However, there are problems with this method of treatment. For example, the masking effect is temporary. When the device is turned off or removed, suppression is ended and the tinnitus percept returns very quickly. Another problem with this treatment is that the patient suffers from a loss of environmental awareness while employing the sound treatment. In this regard, the fact that the technology employed requires the blocking of the ear canal in order to deliver the masking sound into the ears means that other environmental sounds are blocked or at least muted to some degree. This can create problems for simple tasks such as crossing the street or listening to colleagues during a meeting. Thus, this type of treatment often requires the suppression to be turned off (or the devices to be removed) during encounters with many common environments or situations, which can occur on a daily basis.

Accordingly, it may be desirable to provide an improved device for treatment of tinnitus, that is less obtrusive and can avoid interference with environmental awareness. Doing so could provide the significant advantage of enabling the device to be worn much more frequently, if not at all times.

BRIEF SUMMARY OF SOME EXAMPLES

Some example embodiments may enable the provision of a device capable of treating tinnitus without interfering with normal hearing.

In one example embodiment, a tinnitus treatment device is provided. The tinnitus treatment device may include a sound generation unit configured to generate an electrical stimulus, and an open earphone operably coupled to the sound generation unit to produce acoustic vibrations based on the electrical stimulus. The open earphone may include an auditory passage and the open earphone may be insertable into an ear canal of a person such that the auditory passage enables sound to pass substantially unobstructed by the device into the ear canal of the person. The sound generation unit may be configured to be adjustable to tune the electrical stimulus based on a characteristic of tinnitus symptoms experienced by the person.

In another example embodiment, an open earphone for a tinnitus treatment device is provided. The open earphone may include an acoustic driver configured to produce acoustic vibrations based on an electrical stimulus, the acoustic driver comprising a piezoelectric ring having a substantially annular shape with a hollow center, and a pliable retainer defining an auditory passage. The pliable retainer may be operably coupled to the acoustic driver such that the hollow center of the annular shape is substantially aligned with the auditory passage to enable sound to pass substantially unobstructed by the open earphone into an ear canal of a person wearing the open earphone by inserting the pliable retainer into the ear canal.

In still another example embodiment, a method of treating tinnitus is provided. The method may include providing an open earphone having an auditory passage for insertion into an ear canal of a person being treated for tinnitus such that the auditory passage enables sound to pass substantially unobstructed by the open earphone into the ear canal of the person. The method may further include operably coupling the open earphone to a sound generation unit configured to generate an electrical stimulus that drives the open earphone and tuning the sound generation unit to generate acoustic vibrations based on the electrical stimulus. In the context of the method above, the electrical stimulus may be tuned based on a characteristic of tinnitus symptoms experienced by the person.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Figure 1:
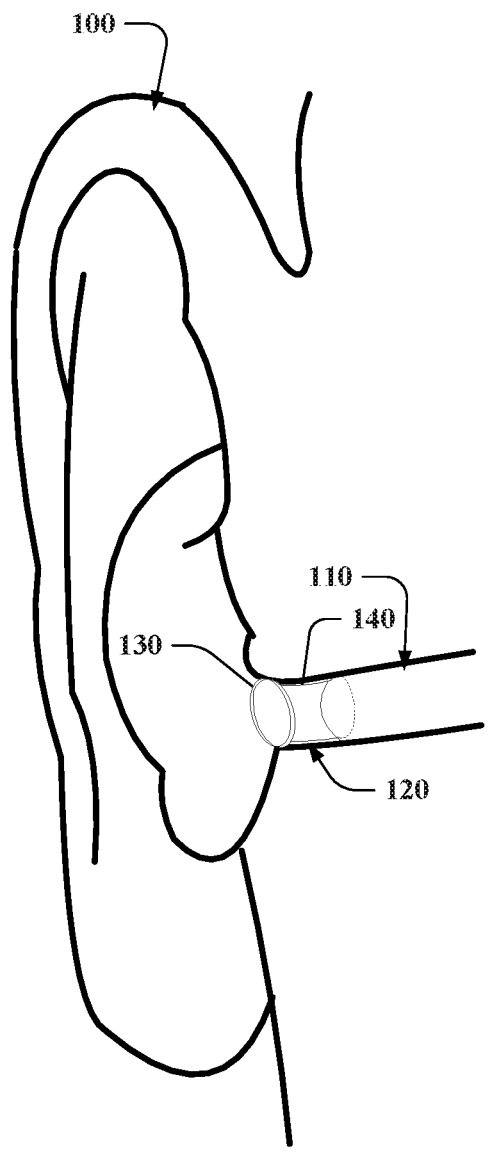
FIG. 1 illustrates a conceptual view of the ear of a patient employing an open earphone for tinnitus treatment from a front perspective in accordance with an example embodiment.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. Furthermore, as used herein, the term "or" is to be interpreted as a logical operator that results in true whenever one or more of its operands are true. Additionally, the term "operable coupling" should be understood to relate to direct or indirect connection that, in either case, enables functional interconnection of components that are operably coupled to each other.

Based on the descriptions above, it can be appreciated that an improved device for treatment of tinnitus would be less obtrusive and avoid interference with environmental awareness. Example embodiments may provide such a device by using a structure, and materials that enable the use of the structure, that is capable of delivering effective treatment without blocking the ear canal of the patient. In this regard, example embodiments may employ materials that support the provision of a personal sound generator or modulator that provides therapeutic treatments to patients suffering from tinnitus via an acoustic driver that has the shape of an open ring capable of fitting into the ear of a patient without blocking the ear canal. In some cases, piezoelectric materials having special mechanical properties that facilitate forming the materials into the open ring shape are employed. An example of such piezoelectric materials includes a polymeric piezoelectric film or fiber such as Poly (Gamma-Benzyl, Alpha, L-Glutamate), which is referred to as PBLG. Detailed descriptions of PBLG are included in U.S. Pat. Nos. 8,641,919 and 9,484,524, which share a common inventor with the present disclosure, and each of which is incorporated herein by reference in their entirety.

By using PBLG (or similar) material, the open ring shaped acoustic driver may be incorporated into an open tube device that can comfortably and effectively fit into the ear of the patient without being obstructive to environmental sounds. The resulting device can be removable for cleaning or repair, but is also configured to be tailored to the individual patient and the patient's unique tinnitus characteristics. Thus, the type of tailoring includes sizing or fitting the open tube structure to the individual, and tuning the acoustic driver to the best or most effective frequency for treating the individual. Accordingly, for example, clinicians may be able to determine the characteristic frequencies of an individual patient's symptoms, and tune the acoustic driver accordingly. Moreover, the clinician may be able to adjust the tuning of the acoustic driver, if needed. As such, tinnitus treatments can be effectively delivered to patients without causing any appreciable loss in environmental awareness.

Figure 2:
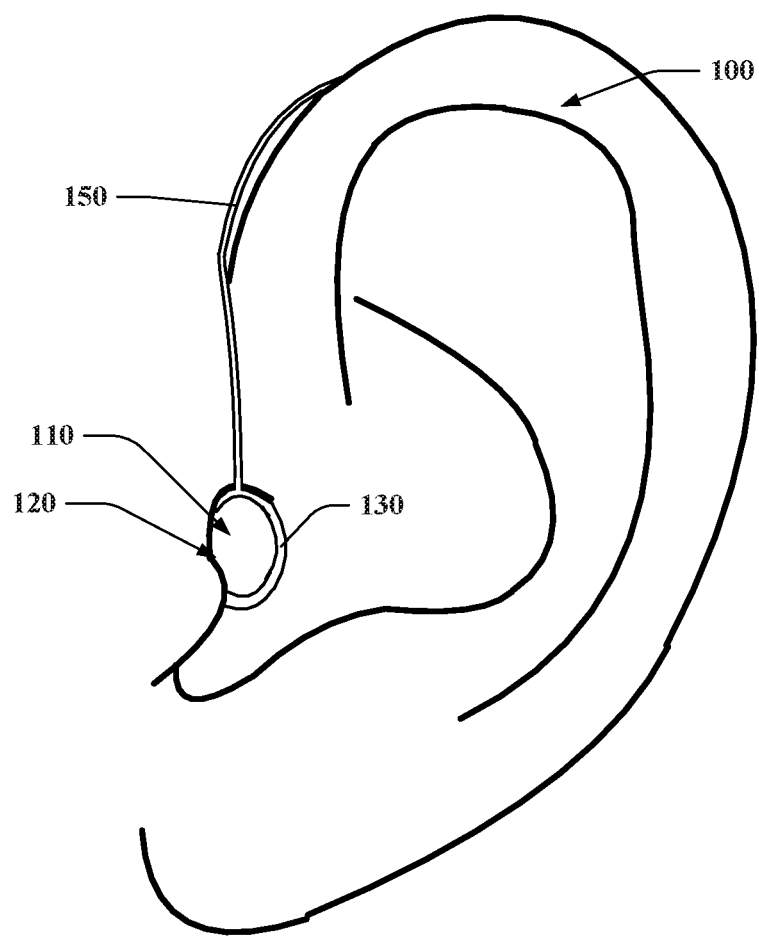
FIG. 2 illustrates the open earphone of FIG. 1 from a side perspective in accordance with an example embodiment.

FIGS. 1 and 2 illustrate front and side conceptual views of the ear of a patient employing a device in accordance with an example embodiment. In this regard, as shown in FIG. 1, an outer ear 100 and ear canal 110 may direct sound energy in toward the middle ear and inner ear of the patient. Thereafter, several parts of the middle ear and inner ear (not shown) transfer sound to the brain. In this regard, for example, the sound energy proceeds from the ear canal 110 to the ear drum so that movement at the ear drum can be transferred to the malleus (or hammer). The malleus then transfers sound energy to the incus (or anvil), which further transfers the sound energy to the stapes (or stirrup). From the stapes, sound energy is transferred to the chochlea or inner ear, where the sound pressure patterns are converted to electrical impulses that can be transmitted to the brain via the auditory nerve.

A conventional hearing aid typically includes an in-line microphone that is inserted in the ear canal 110 to amplify sounds that are headed toward the ear drum. Conventional tinnitus treatment devices follow a similar conceptual arrangement, and therefore include an in-line sound generating device as a suppressor. However, rather than simply amplifying sound headed to the ear drum, tinnitus treatment devices would need to be configured to generate some masking frequency or sound, to reduce the sensitivity to the perception of tinnitus. Thus, the ear canal 110 is necessarily blocked during treatment, and the issues described above are created, thereby limiting the utility of such devices.

Figure 3:
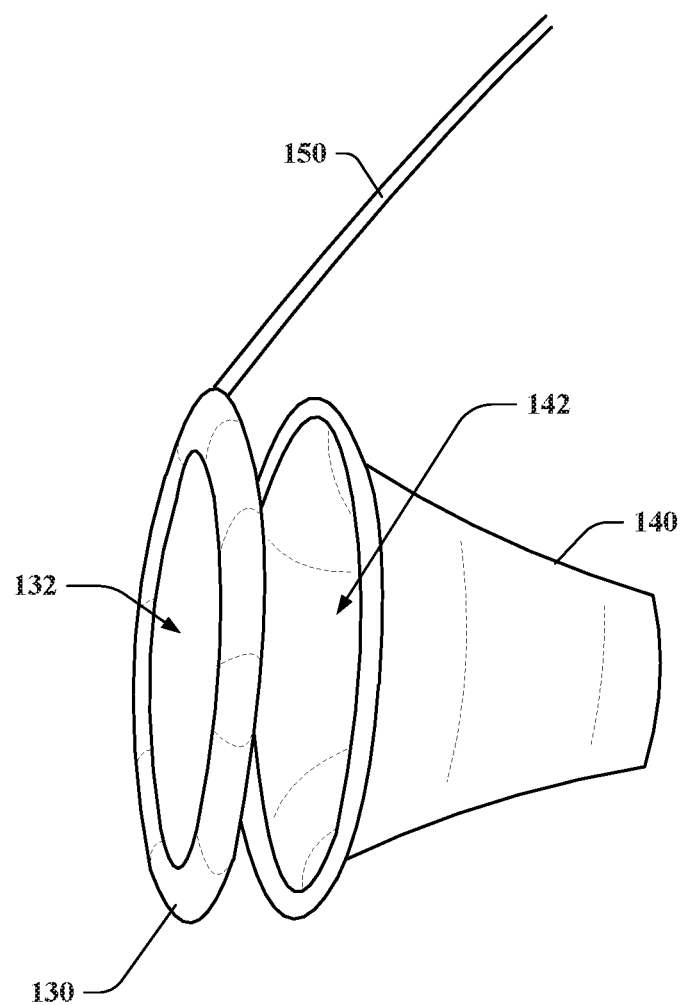
FIG. 3 illustrates an isolated perspective view of the open earphone in accordance with an example embodiment.
Figure 4:
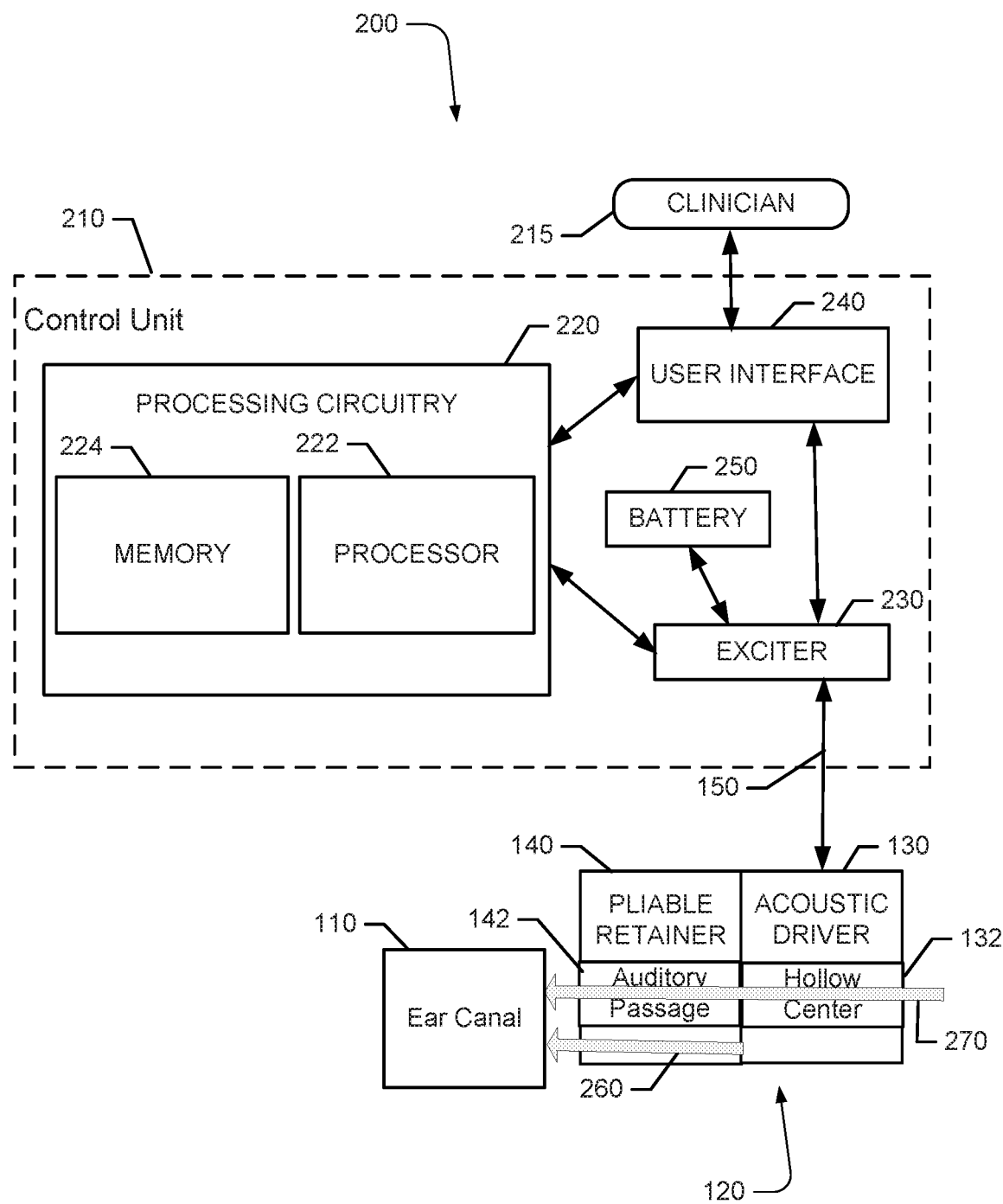
FIG. 4 illustrates a block diagram of a tinnitus treatment device in accordance with an example embodiment.

In an example embodiment, an open earphone 120 is employed, which does not block the ear canal 110. In this regard, for example, the open earphone includes an acoustic driver 130 and a pliable retainer 140. A more detailed view of the acoustic driver 130 and the pliable retainer 140 of an example embodiment are shown in FIG. 3. Meanwhile, FIG. 4 illustrates a block diagram of various components of a tinnitus treatment device 200 that may include the open earphone 120 of FIGS. 1-3.

In an example embodiment, the acoustic driver 130 may be configured to produce acoustic vibrations based on an electrical stimulus. In particular, as shown in FIG. 3, for example, the acoustic driver 130 may be formed as a piezoelectric ring having a substantially annular shape with a hollow center 132. The hollow center 132 ensures that environmental sound can still (i.e., when the open earphone 120 is worn by a person seeking treatment) enter the ear canal 110 with relatively little obstruction so that hearing relative to sounds generated in the external environment is generally not impacted (or at least the impact is relatively small). However, the inclusion of the hollow center 132, and the annular shape of the acoustic driver 130 represents a physical limitation that can be challenging to overcome.

As such, finding a suitable material that can act as the acoustic driver 130 is a nontrivial undertaking. In this regard, the material must be capable of manufacture on the relatively small scales needed to correspond to the size of human ear canals. However, the material must also be capable of manufacture to the desired size while still having special mechanical properties that permit use as an acoustic material. Additionally, the small scale and special mechanical properties must exist while also allowing the annular shape to be employed. As such, materials that require a large (in terms of thickness or diameter) size or cannot be formed in the annular shape will not be suitable for use in example embodiments.

Example embodiments may therefore employ polymeric piezoelectric fibers or films that have the special mechanical properties necessary to produce acoustic vibrations in response to the electrical stimulus. However, the polymeric piezoelectric fibers or films employed must also have the mechanical strength and flexibility to enable relatively easy manufacture of the piezoelectric ring. In an example embodiment, the material used to form the piezoelectric ring may include Poly (γ-benzyl α, L-glutamate) (PBLG) film or fiber. The PBLG material generally has the ability to produce acoustic vibrations in response to electrical stimuli with a low-frequency response. The PBLG material also has micron-scale functionality that makes the PBLG material suitable for use in the size and shape requirements necessary to support use in a device scaled for the human ear canal. Additionally, the PBLG material has substrate independence (e.g., the material is not limited to a specific shape). This substrate independence may provide a relative freedom with respect to physical specifications that enables multiple sizes and shapes to be used for the acoustic driver 130, which means the acoustic driver 130 (and the pliable retainer 140) can be manufactured to be of different dimensions, sizes, shapes, etc., so that individuals can be sized for a properly or comfortably fitting open earphone 120.

The substrate independence may also provide the ability for the piezoelectric ring of the acoustic driver 130 to be formed either from a solution in an annular shaped mould, or formed (e.g., via electrospinning) onto an annular shaped substrate. In some example embodiments, the PBLG material used to form the piezoelectric ring may be fabricated by electrospinning a PBLG/dichloromethane (DCM) solution under a potential of about 12 to 15 kV. The resultant fibers may have high piezoelectricity and an elastic modulus of about 570 MPa. As described in U.S. Pat. Nos. 8,641,919 and 9,484,524, the PBLG fibers of the piezoelectric ring may be formed to have substantially all of the dipoles thereof oriented along a fiber axis. In some example embodiments, the PBLG material may employ a film or fiber structure having a thickness of about 40 microns to form the piezoelectric ring. However, other dimensions (larger or smaller) can also be employed in some cases. The acoustic driver 130 may have an upper frequency response of about 10 kHz and a maximum sound output of 80 dB sound pressure level.

The pliable retainer 140 may also be made from a flexible material that can be molded to fit multiple shapes or sizes. In particular, the pliable retainer 140 may be molded of resin material that can be comfortably fit within the ear canal 110, but may be removed and cleaned or otherwise maintained routinely. In an example embodiment, the pliable retainer 140 may be formed to define an auditory passage 142 that passes through an axial center thereof. As such, the structure of the pliable retainer 140 may be similar to that of a drinking straw, which means that a thin outer sheath of material forms a tubular structure that is hollow. Materials that may be used to form the pliable retainer 140 may include mechanically compliant blends such as elastomers, polymeric materials (e.g., polypropylene variants), and polymeric composites (e.g., blends of stiff and stretchable materials). In some cases, additively manufactured materials may be used to form the pliable retainer 140 as such materials would allow tuning or optimization of material properties during production so that, for example, feature sizes that are a closer match to the dimensions of the ear of different patients can be mass produced. The thickness of the material used to form the pliable retainer 140 may be many times less than the diameter of the pliable retainer 140. For example, the thickness of the material used to form the pliable retainer 140 may be less than 20% of the diameter of the pliable retainer 140. However, even thinner materials may be desired in some cases. Thus, in some examples, the thickness of the material used to form the pliable retainer 140 may be less than 10% of the diameter of the pliable retainer 140 or even less than 5%.

The ratio of the thickness of the annular shape used for form the piezoelectric ring to the diameter of the acoustic driver 130 may substantially match the ratio of the thickness of the material used to form the pliable retainer 140 to the diameter of the pliable retainer 140. Thus, when the acoustic driver 130 is operably coupled to the pliable retainer 140, the corresponding materials thereof may substantially overlap so that an adhesive or other bonding material may effectively hold the acoustic driver 130 and the pliable retainer 140 in contact with each other. Snap fitting, press fitting, or other mechanical joining methods could also be used in some embodiments. Making the sizes correspond also has the benefit of aligning the auditory passage 142 with the hollow center 132. In some cases, the diameter of the auditory passage 142 may reduce (as shown in FIG. 3) as distance from the acoustic driver 130 increases. However, the diameter could alternatively stay relatively consistent along the entire or majority of the length of the pliable retainer 140 in other cases. The differences in diameter may be made to accommodate different ear canals of potential patients.

As can be appreciated from FIGS. 1-3, operably coupling the pliable retainer 140 to the acoustic driver 130 such that the hollow center 132 is substantially aligned with the auditory passage 142 will prevent blocking the ear canal 110 while a person wearing the open earphone 120 has the open earphone 120 in his/her ear in the manner shown in FIGS. 1 and 2. Thus, sound may be allowed to pass substantially unobstructed by the open earphone 120 into the ear canal 110 (i.e., through the hollow center 132 of the acoustic driver 130 and the auditory passage 142 of the pliable retainer 140) and environmental awareness can be preserved, even while wearing and operating the open earphone 120. In other words, at least 50% of the diameter of the ear canal may remain open an unblocked by any structure even while the open earphone 120 is being worn. Thus, the openness of the ear canal 110 is preserved even while acoustic vibrations are actively being generated by the acoustic driver 130. The acoustic vibrations generated by the acoustic driver 130 may be programmed to have frequencies that are tuned to treat tinnitus. Thus, the acoustic vibrations generated by the acoustic driver 130 may be transmitted into the ear of the person wearing the open earphone 120 and be perceived by the brain as a tinnitus masking sound without interfering with environmental sound being also perceived by the brain through the normal operation of the ear.

The programming of acoustic vibrations to be generated by the acoustic driver 130 may be accomplished at a control unit 210, which may be operably coupled to the acoustic driver 130 via a wired connection 150. The wired connection 150 may extend from the electrodes that are coupled to the fibers or film of the acoustic driver 130 to the control unit 210, as shown in the block diagram of FIG. 4. In this regard, FIG. 4 illustrates a block diagram of a tinnitus treatment device 200 for use while minimizing any interference with environmental awareness in accordance with an example embodiment. As shown in FIG. 4, the tinnitus treatment device 200 may include the control unit 210 and the open earphone 120 along with the wired connection 150 operably connecting the control unit 210 and the open earphone 120 to each other.

In an example embodiment, the control unit 210 may be provided to control and/or coordinate operation of the tinnitus treatment device 200. As such, for example, the control unit 210 may be used to enable an operator (e.g., a clinician 215) to program (or tune) the operating frequency of the acoustic driver 130. In this regard, for example, the control unit 210 may include processing circuitry 220 configured to control an exciter 230, which provides electrical signals to drive the acoustic driver 130 via the wired connection 150. In this regard, the frequency of the electrical signals generates corresponding vibrations in the acoustic driver 130. In some cases, the control unit 210 may include a user interface 240 that is accessible only by the clinician 215 (i.e., the patient cannot access the user interface 240). The user interface 240 may be a tuner or adjuster that is configured to interface with the exciter 230 to alter the voltage, frequency and/or pattern of signals that are applied to the exciter 230. The exciter 230 (and the control unit 210 generally) may be powered by a battery 250 or other power source, and may generate potentials based on programming and/or settings applied thereto. In some cases, the user interface 240 may directly be used to interface with the exciter 230 to adjust a frequency output of the exciter 230. However, in other cases, the user interface 240 may be operated to interface with the processing circuitry 220 to employ programs that can be executed by a processor 222 of the processing circuitry 220 responsive to storage of the programs in memory 224. Thus, it should be appreciated that the control unit 210 may be embodied as a relatively simple circuit or device that enables direct control of the exciter 230 by the user interface 240. Alternatively, the control unit 210 may be embodied as a more complicated control device that includes programs that can be selected for execution by the clinician 215.

If employed, the processing circuitry 220 may be configured to perform data processing, control function execution and/or other processing and management services according to an example embodiment of the present invention. In some embodiments, the processing circuitry 220 may be embodied as a chip or chip set. In other words, the processing circuitry 220 may comprise one or more physical packages (e.g., chips) including materials, components and/or wires on a structural assembly (e.g., a baseboard).

In an example embodiment, the processing circuitry 220 may include one or more instances of the processor 222 and memory 224 that may be in communication with or otherwise control the exciter 230. As such, the processing circuitry 220 may be embodied as a circuit chip (e.g., an integrated circuit chip) configured (e.g., with hardware, software or a combination of hardware and software) to perform operations described herein. The processing circuitry 220 may further interface with the user interface 240 as described above.

In an exemplary embodiment, the memory 224 may include one or more non-transitory memory devices such as, for example, volatile and/or non-volatile memory that may be either fixed or removable. The memory 224 may be configured to store information, data, applications, instructions or the like for enabling the processing circuitry 220 to carry out various functions in accordance with exemplary embodiments of the present invention. For example, the memory 224 could be configured to buffer input data for processing by the processor 222. Additionally or alternatively, the memory 224 could be configured to store instructions for execution by the processor 222. As yet another alternative, the memory 224 may include one or more databases that may store a variety of excitation patterns and/or data sets indicative of specific signals for input to the exciter 230 to generate excitation for the acoustic driver 130 to be employed for the execution of example embodiments. Among the contents of the memory 224, applications may be stored for execution by the processor 222 in order to carry out the functionality associated with each respective application. In some cases, the applications may include directions for control of the exciter 230 to generate frequencies or patterns of vibration in accordance with a selected one of the applications.

The processor 222 may be embodied in a number of different ways. For example, the processor 222 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor 222 may be configured to execute instructions stored in the memory 224 or otherwise accessible to the processor 222. As such, whether configured by hardware or by a combination of hardware and software, the processor 222 may represent an entity (e.g., physically embodied in circuitry—in the form of processing circuitry 220) capable of performing operations according to embodiments of the present invention while configured accordingly. Thus, for example, when the processor 222 is embodied as an ASIC, FPGA or the like, the processor 222 may be specifically configured hardware for conducting the operations described herein. Alternatively, as another example, when the processor 222 is embodied as an executor of software instructions, the instructions may specifically configure the processor 222 to perform the operations described herein.

In an example embodiment, the processor 222 (or the processing circuitry 220) may be embodied as, include or otherwise control the modules of the control unit 210. As such, in some embodiments, the processor 222 (or the processing circuitry 220) may be said to cause each of the operations described in connection with the modules of the control unit 210 to undertake the corresponding functionalities responsive to execution of instructions or algorithms configuring the processor 222 (or processing circuitry 220) accordingly.

The user interface 240 (if implemented—or when connected) may be in communication with the processing circuitry 220 and/or exciter 230 to receive an indication of a user input (e.g., from the clinician 215) at the user interface 240. As such, if the user interface 240 is a permanent or internal component of the control unit 210, the user interface 240 may include, for example, one or more buttons, dials, levers, tuners, and/or the like. However, if the user interface 240 may include an external input/output mechanism (e.g., keyboard, display, touch screen, mouse, microphone, speakers, cursor, joystick, lights and/or the like). When the user interface 240 is embodied as an external input/output mechanism, the user interface 240 may be separable from the rest of the control unit 210 and only temporarily connected thereto (e.g., for making adjustments to the exciter 230). Alternatively, the user interface 240 could be at a completely separate device and may interface with the processing circuitry 220 and/or the exciter 230 wirelessly. Thus, a remote terminal could be used for tuning in some cases. The user interface 240, particularly when embodied as an external input/output mechanism, may also generate information indicative of the program selected or the expected output operating frequency or vibrational pattern that is to be generated by the exciter 230.

The exciter 230 is configured to apply the electrical stimulus to the acoustic driver 130 based on input selections made by the clinician 215 at the user interface 240. Responsive to the electrical stimulus being provided to the acoustic driver 130, the acoustic driver 130 may generate acoustic vibrations 260 that enter the ear canal 110 directly and/or via the pliable retainer 140. In this regard, for example, the fibers of the acoustic driver 130 may compress responsive to the application of the electrical stimulus to generate the acoustic vibrations 260. In some cases, the extension of the pliable retainer 140 into the ear canal 110 may further facilitate distributed contact with the ear canal 110 for better conduction of the acoustic vibrations 260. In all cases, the alignment of the auditory passage 142 with the hollow center 132 of the piezoelectric ring of the acoustic driver 130 allows environmental sound 270 to enter into the ear canal 110 relatively unobstructed.

As mentioned above, the open earphone 120 may be removable for cleaning and/or maintenance. The maintenance may include adjustment of the exciter 230 to improve or adjust the therapy being provided via the control unit 210. In this regard, the exciter 230 may be providing a specific masking frequency that may be selected by the clinician 215 based on known characteristics of the tinnitus experienced by the patient wearing the tinnitus treatment device 200. In some cases, the tinnitus experienced by the patient may be characterized (e.g., on a spectrum) and the clinician 215 may select masking or treatment frequencies to be applied based on the characterized tinnitus of each respective individual patient. Thereafter, depending on performance evaluations provided by the patient, adjustments may be made by the clinician 215 to improve performance and effectiveness.

Figure 5:
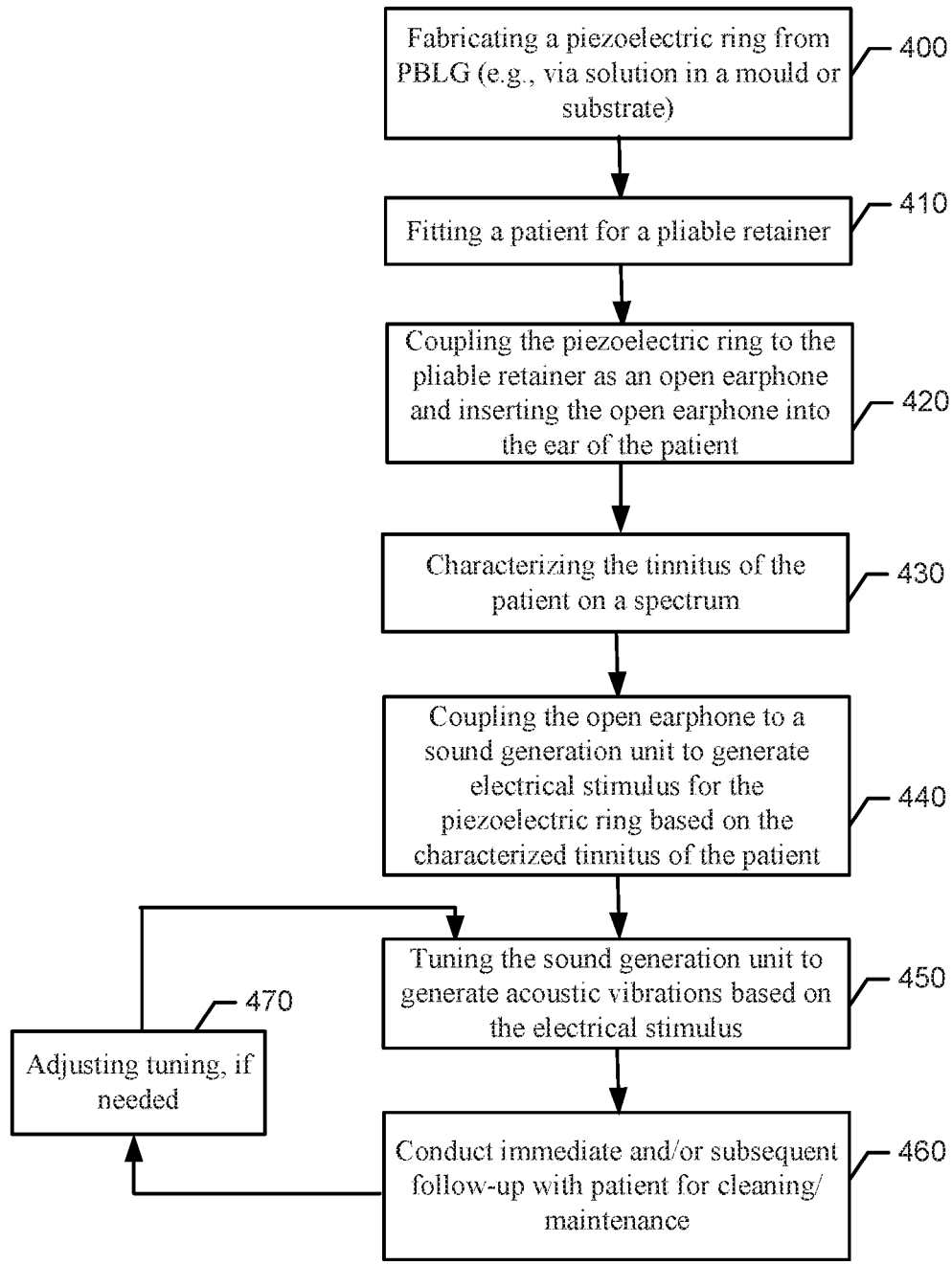
FIG. 5 illustrates a block diagram of a method of employing a tinnitus treatment device for providing tinnitus treatment without interfering with environmental awareness in accordance with an example embodiment.

FIG. 5 illustrates a block diagram of a method of providing tinnitus treatment using a treatment device of an example embodiment. As shown in FIG. 5, the method may include fabricating a piezoelectric ring from PBLG at operation 400. The fabrication may be conducted via solution in a mould or on a substrate by electrospinning, as discussed above. The method may further include fitting a patient for a pliable retainer at operation 410. The patient may, for example, try on various sizes/shapes/models in order to select a comfortable pliable retainer for the patient. The method may further include coupling the piezoelectric ring to the pliable retainer to form an open earphone, and inserting the open earphone into the ear of the patient at operation 420. Generally speaking, operations 400 to 420 may be summarized as providing an open earphone having an auditory passage for insertion into an ear canal of a person being treated for tinnitus such that the auditory passage enables sound to pass substantially unobstructed by the open earphone into the ear canal of the person.

The method may further include characterizing the tinnitus of the patient (e.g., on a spectrum) at operation 430, and operably coupling the open earphone to a sound generation unit (e.g., the control unit 210 and/or the exciter 230) configured to generate an electrical stimulus that drives the open earphone at operation 440. The method may further include tuning the sound generation unit to generate acoustic vibrations based on the electrical stimulus at operation 450. Thereafter, follow-up may be conducted with the patient for cleaning or maintenance at operation 460. If needed, additional tuning may be conducted at operation 470.

Example embodiments therefore represent a design for a tinnitus treatment device. The tinnitus treatment device may include a sound generation unit configured to generate an electrical stimulus, and an open earphone operably coupled to the sound generation unit to produce acoustic vibrations based on the electrical stimulus. The open earphone may include an auditory passage and the open earphone may be insertable into an ear canal of a person such that the auditory passage enables sound to pass substantially unobstructed by the device into the ear canal of the person. The sound generation unit may be configured to be adjustable to tune the electrical stimulus based on a characteristic of tinnitus symptoms experienced by the person.

In some embodiments, additional optional structures and/or features may be included or the structures/features described above may be modified or augmented. Each of the additional features, structures, modifications or augmentations may be practiced in combination with the structures/features above and/or in combination with each other. Thus, some, all or none of the additional features, structures, modifications or augmentations may be utilized in some embodiments. Some example additional optional features, structures, modifications or augmentations are described below, and may include, for example, the fact that the open earphone may include an acoustic driver configured to produce acoustic vibrations based on the electrical stimulus and a pliable retainer defining the auditory passage. The acoustic driver may include a piezoelectric ring having a substantially annular shape with a hollow center. In an example embodiment, the piezoelectric ring may include Poly (γ-benzyl α, L-glutamate) (PBLG) film or fiber. Additionally or alternatively, the PBLG may be fabricated by electrospinning a PBLG/dichloromethane (DCM) solution under a potential of about 12 to 15 kV. Additionally or alternatively, the piezoelectric ring may include PBLG fibers formed to have substantially all dipoles thereof oriented along a fiber axis. Additionally or alternatively, the piezoelectric ring may include PBLG fibers formed from a solution in an annular shaped mould. Additionally or alternatively, the piezoelectric ring may include PBLG fibers formed from a solution on an annular shaped substrate.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. A tinnitus treatment device comprising:
    a sound generation unit configured to generate an electrical stimulus;
    an open earphone operably coupled to the sound generation unit to produce acoustic vibrations based on the electrical stimulus, wherein the open earphone includes an auditory passage and the open earphone is insertable into an ear canal of a person such that the auditory passage enables sound to pass substantially unobstructed by the device into the ear canal of the person; and
    an acoustic driver configured to produce acoustic vibrations based on the electrical stimulus, the acoustic driver comprising a piezoelectric ring having a substantially annular shape with a hollow center, wherein the sound generation unit is configured to be adjustable to tune the electrical stimulus based on a characteristic of tinnitus symptoms experienced by the person.

2. The device of claim 1, wherein the open earphone comprises:
    a pliable retainer defining the auditory passage.

3. The device of claim 1, wherein the piezoelectric ring comprises Poly (γ-benzyl α, -glutamate) (PBLG) film or fiber.

4. The device of claim 3, wherein the PBLG is fabricated by electrospinning a PBLG/dichloromethane (DCM) solution under a potential of about 12 to 15 kV.

5. The device of claim 3, wherein the piezoelectric ring comprises PBLG fibers formed to have substantially all dipoles thereof oriented along a fiber axis.

6. The device of claim 3, wherein the piezoelectric ring comprises PBLG fibers formed from a solution in an annular shaped mould.

7. The device of claim 3, wherein the piezoelectric ring comprises PBLG fibers formed from a solution on an annular shaped substrate.

8. An open earphone for a tinnitus treatment device, the open earphone comprising:
   an acoustic driver configured to produce acoustic vibrations based on an electrical stimulus, the acoustic driver comprising a piezoelectric ring having a substantially annular shape with a hollow center; and
   a pliable retainer defining an auditory passage,
   wherein the pliable retainer is operably coupled to the acoustic driver such that the hollow center of the annular shape is substantially aligned with the auditory passage to enable sound to pass substantially unobstructed by the open earphone into an ear canal of a person wearing the open earphone by inserting the pliable retainer into the ear canal.

9. The open earphone of claim 8, wherein the piezoelectric ring comprises Poly (Gamma-Benzyl, Alpha, L-Glutamate) (PBLG) film or fiber.

10. The open earphone of claim 9, wherein the PBLG is fabricated by electrospinning a PBLG/dichloromethane (DCM) solution under a potential of about 12 to 15 kV.

11. The open earphone of claim 9, wherein the piezoelectric ring comprises PBLG fibers formed to have substantially all dipoles thereof oriented along a fiber axis.

12. The open earphone of claim 9, wherein the piezoelectric ring comprises PBLG fibers formed from a solution in an annular shaped mould.

13. The open earphone of claim 9, wherein the piezoelectric ring comprises PBLG fibers formed from a solution on an annular shaped substrate.

14. A method of treating tinnitus comprising:
   providing an open earphone having an auditory passage for insertion into an ear canal of a person being treated for tinnitus such that the auditory passage enables sound to pass substantially unobstructed by the open earphone into the ear canal of the person;
   operably coupling the open earphone to a sound generation unit configured to generate an electrical stimulus that drives the open earphone;
   forming an acoustic driver configured to produce acoustic vibrations based on the electrical stimulus, the acoustic driver comprising a piezoelectric ring having a substantially annular shape with a hollow center; and
   tuning the sound generation unit to generate the acoustic vibrations based on the electrical stimulus, wherein the electrical stimulus is tuned based on a characteristic of tinnitus symptoms experienced by the person.

15. The method of claim 14, wherein providing the open earphone comprises:
   operably coupling the acoustic driver to a pliable retainer defining the auditory passage.

16. The method of claim 14, wherein forming an acoustic driver comprises forming the piezoelectric ring from Poly (Gamma-Benzyl, Alpha, L-Glutamate) (PBLG) film or fiber.

17. The method of claim 16, wherein the PBLG is fabricated by electrospinning a PBLG/dichloromethane (DCM) solution under a potential of about 12 to 15 kV.

18. The method of claim 16, wherein forming the piezoelectric ring from PBLG comprises forming PBLG fibers to have substantially all dipoles thereof oriented along a fiber axis.

19. The method of claim 16, wherein forming the piezoelectric ring from PBLG comprises forming PBLG fibers from a solution in an annular shaped mould.

20. The method of claim 16, wherein forming the piezoelectric ring from PBLG comprises forming PBLG fibers from a solution on an annular shaped substrate.

* * * * *